United States Patent
Chaudhuri

(10) Patent No.: US 9,359,584 B2
(45) Date of Patent: Jun. 7, 2016

(54) MICROBIAL ENZYMES AS DETERGENT ADDITIVES

(75) Inventor: Shaon Ray Chaudhuri, Kolkata (IN)

(73) Assignee: WEST BENGAL UNIVERSITY OF TECHNOLOGY, Kolkata (IN)

(*) Notice: Subject to any disclaimer, the term of this patent is extended or adjusted under 35 U.S.C. 154(b) by 0 days.

(21) Appl. No.: 13/126,109

(22) PCT Filed: Jul. 24, 2010

(86) PCT No.: PCT/IB2010/001816
§ 371 (c)(1),
(2), (4) Date: Apr. 26, 2011

(87) PCT Pub. No.: WO2011/151666
PCT Pub. Date: Dec. 8, 2011

(65) Prior Publication Data
US 2012/0021489 A1    Jan. 26, 2012

(30) Foreign Application Priority Data
Jun. 1, 2010  (IN) .............................. 599/KOL/2010

(51) Int. Cl.
| | | |
|---|---|---|
| C11D 3/386 | (2006.01) | |
| C12N 9/20 | (2006.01) | |
| C12N 9/28 | (2006.01) | |
| C12N 9/52 | (2006.01) | |

(52) U.S. Cl.
CPC ............ *C11D 3/386* (2013.01); *C11D 3/38681* (2013.01); *C12N 9/20* (2013.01); *C12N 9/2417* (2013.01); *C12N 9/52* (2013.01)

(58) Field of Classification Search
None
See application file for complete search history.

(56) References Cited

U.S. PATENT DOCUMENTS

| | | | |
|---|---|---|---|
| 5,618,465 A | 4/1997 | Durbut et al. | |
| 2002/0187541 A1* | 12/2002 | Leung et al. | ................... 435/202 |
| 2003/0068791 A1* | 4/2003 | Miasnikov et al. | ........... 435/158 |

FOREIGN PATENT DOCUMENTS

| | | |
|---|---|---|
| CN | 86106566 | 4/1988 |
| CN | 101522878 | 4/2008 |
| WO | WO-2008/040818 | 4/2008 |

OTHER PUBLICATIONS

Gessesse, A., et al., 1997, "Production of alkaline protease by an alkaliphilic bacteria isolated from an alkaline soda lake", Biotechnology Letters, vol. 19, No. 5, pp. 479-481.*
Thys, R. C. S., et al., 2006, "Purification and properties of a keratinolytic metalloprotease from Microbacterium sp.", Journal of Applied Microbiology, vol. 101, No. 6, pp. 1259-1268.*
Banik. R.M. and Prakash, M. "Laundry Detergent Compatibility of the Alkaline Protease from *Bacillus cereus*," Micro biol. Res., vol. 159, No. 2, pp. 135-140, 2004.
Chand S. and Mishra P., "Research and Application of Microbial Enzymes-India's Contribution," Advances in Biochemical Engineering Biotechnology, vol. 85, pp. 95-124, 2003.

(Continued)

*Primary Examiner* — Manjunath Rao
*Assistant Examiner* — William W Moore
(74) *Attorney, Agent, or Firm* — Foley & Lardner LLP

(57) ABSTRACT

Provided in part herein are compositions that include isolated microbial enzymes, such as amylases, lipases, and proteases that are useful as detergent additives. Also provided are methods of isolating amylases, lipases, and proteases from microbes, as well as methods of using these enzymes as detergent additives, and for stain removal.

8 Claims, 10 Drawing Sheets

A

B

(56) References Cited

OTHER PUBLICATIONS

Chaudhuri, S. and Thakur, A.R., "Microbial Genetic Resource Mapping of East Calcutta Wetland," Curr. Sci., vol. 91, pp. 212-217, 2006.
Chaudhuri, S., et al., "Role of Water Hyacinth Mediated Phytoremediation in Waste Water Purification at East Calcutta Wetland," Environ. Sci., vol. 5, pp. 53-62, 2008.
Chowdhury, S., et al., "Novel Metal Accumulator and Protease Secretor Microbes from East Calcutta Wetland," American Journal of Biochemistry and Biotechnology, vol. 4, pp. 255-264, 2008.
Hasan, F., et al., "Industrial Applications of Microbial Lipases". Enzyme Microbial. Technol., vol. 39, pp. 235-251, 2006.
Howe, T.R. and Iglewski, B.H., "Isolation and Characterization of Alkaline Protease-Deficient Mutants of *Pseudomonas aeruginosa* in Vitro and in a Mouse Eye Model," Infect. Immunity, 43, vol. 3, pp. 1058-1063, 1984.
http://www.specialtyenzymes.com/detergents.htm "The use of enzymes in detergents," accessed online at: http://www.lsbu.ac.uk/biology/enztech/detergent.html on May 25, 2012, page last updated on Dec. 20, 2004, pp. 1-3.
Moreira, K.A., et al., "Application of Protease from *Nocardiopsis* sp. as a Laundry Detergent Additive," World J. Microbial. Biotechnol., vol. 18, No. 4, pp. 309-315(7), 2002.
Najafi, M.F., et al., "Potential Application of Protease Isolated from *Pseudomonas aeruginosa* PD100," Electronic J. Biotechnol., vol. 8, No. 2, pp. 197-203, 2005.
Nascimento, W.C.A. and Martins, M.L.L., 01CStudies on the Stability of Protease from *Bacillus* sp. and its Compatibility with Commercial Detergent, Brazilian J. Microbiol., vol. 37, pp. 307-311, 2006.
Oberoi, R., et al., "Characterization and Wash Performance Analysis of an SDS Stable Alkaline Protease from a *Bacillus* sp.," World J. Microbial. Biotechnol., vol. 17, No. 5, pp. 493-497, 2001.
Rao, M.B., et al., "Molecular and Biotechnological Aspects of Microbial Proteases." Microbiol. Molecular Biol. Rev., vol. 62, No. 3, pp. 597-635, Sep. 1998.
Raychaudhuri, S., et al., "Integrated Resource Recovery at East Calcutta Wetland-How Safe is These?" Am. J. Agric. Biol. Sci., vol. 2, pp. 75-80, 2007.
Raychaudhuri, S., et al., "Waste Management: A Case Study of Ongoing Traditional Practices at East Calcutta Wetland," Am. J. Agric. Biol. Sci., vol. 3, pp. 315-320, 2008.
Raychaudhuri, S., et al., "Traditional Aquaculture Practice at East Calcutta Wetland: The Safety Assessment," Am. J. Environ. Sci., vol. 4, No. 2, pp. 140-144, 2008.
Ahmed, S.A. et al., "Stabilization of *Bacillus licheniformis* ATCC 21415 Alkaline Protease by Immobilization and Modification," Aust. J. Basic Applied Sci., 2007, vol. 1, No. 3, pp. 313-322.
GenBank Accession No. EU006695, Sep. 11, 2009. Sequence shares 100% identity with SEQ ID No. 1.
GenBank Accession No. FJ377723, Nov. 9, 2008. Sequence shares 100% identity with SEQ ID No. 3.
GenBank Accession No. FJ788517, Apr. 5, 2009. Sequence shares 100% identity with SEQ ID No. 2.
International Search Report and Written Opinion for PCT/IB2010/001816 mailed Nov. 3, 2010.
Ito, S. et al., "Alkaline detergent enzymes from alkaliphiles: enzymatic properties, genetics, and structures," Extremophiles, 1998, vol. 2, No. 3, pp. 185-190.
Ito, S. et al., "Enzymes in Modern Detergents," Methods in Biotechnology, 2005, vol. 17 (Microbial Enzymes and Biotransformations), Chapter 9, pp. 151-163.
Kumar, C.G. et al., "Microbial alkaline proteases: from a bioindustrial viewpoint," Biotechnol. Adv., 1999, vol. 17, pp. 561-594.
Kumar, S.R. et al., "Continuous production of 1-glutaminase by an immobilized marine *Pseudomonas* sp BTMS-51 in a packed bed reactor," Process Biochemistry, May 30, 2003, vol. 38, No. 10, pp. 1431-1436.
Malathu, R. et al., "Characterization and Wash Performance Analysis of Microbial Extracellular Enzymes from East Calcutta Wetland in India," American J. of Appl. Sci., 2008, vol. 5, No. 12, pp. 1650-1661.
Park, I.-H. et al., "Gene Cloning, Purification, and Characterization of a Cold-Adapted Lipase Produced by *Acinetobacter baumannii* BD5," J. of Microbial. and Biotechnol., 2009, vol. 19, No. 2, pp. 128-135.
Pradhan, A. et al., "Phytoplankton Diversity as Indicator of Water Quality for Fish Cultivation," American J. of Environ. Sci., 2008, vol. 4, No. 4, pp. 406-411.
Sarkar, A.D. et al., "Microbial Biodiversity Screening for Metal Accumulators from Mineral Ore Rich Site in Andhra Pradesh, India," OnLine J. of Bio. Sci., 2008, vol. 8, No. 2, pp. 32-40.
Thys, R.C.S. et al., "Characterization of a protease of a feather-degrading Microbacterium species," Letters in Applied Microbiology, 2004, vol. 39, No. 2, pp. 181-186.
Chinese Search Report dated Apr. 9, 2014 in related Chinese Patent Application No. 201180028394.6 Four documents cited in English considered.
Hmidet, Noomen et al., "Alkaline protases and thermostable 3B1-amylase co-produced by Bacillus licheniformis NH1: Characterization and potential application as detergent additive", Biochemical Engineering Journal, 2009, vol. 47, pp. 71-79.
Kiran, Kondepudi Kanthi, "Production of surfactant and detergent-stable, halophilic, and alkalitolerant alpha-amylase by a moderately halophilic Bacillus sp. Strain TSCVKK", Appl. Microbiol Biotechnol, 2008, vol. 77, pp. 1023-1031.
Ningthoujam et al., "Screening, Identification of Best Producers and Optimization of Extracellular Proteases from Moderately Halophilic Alkalithermotolerant Indigenous Actinomycetes", World Applied Sciences Journal, 2009, vol. 7, pp. 907-916.
Sivasubramanian et al., "Two Step Purification of Acinetobacter sp. Lipase and Its Evaluation as a Detergent Additive at Low Temperatures", Appl. Biochem Biotechnol, 2008, vol. 150, pp. 139-156.
Department of the Environment Industry Profile, "Chemical Works—Soap and Detergent Manufacturing Works," 1995, (24 pages) available at https://www.gov.uk/government/uploads/system/uploads/attachment_data/file/290818/scho0195bjkl-e-e.pdf.

\* cited by examiner

A

B

```
                           SEQUENCE LISTING

<160> NUMBER OF SEQ ID NOS: 3

<210> SEQ ID NO 1
<211> LENGTH: 469
<212> TYPE: DNA
<213> ORGANISM: Microbacterium sp.

<400> SEQUENCE: 1
ggatgaacgc tggcggcgtg cttaacacat gcaagtcgaa cggtgaagca ggagcttgct      60
cttgtggatc agtggcgaac gggtgagtaa cacgtgagca acctgcccct gactctggga     120
taagcgctgg aaacggcgtc taatactgga tatgtgacgt gaccgcatgg tctgcgtttg     180
gaaagatttt tcggttgggg atgggctcgc ggcctatcag cttgttggtg aggtaatggc     240
tcaccaaggc gtcgacgggt agccggcctg agagggtgac cggccacact gggactgaga     300
cacggcccag actcctacgg gaggcagcag tggggaatat tgcacaatgg gcgaaagcct     360
gatgcagcaa cgccgcgtga gggatgacgg ccttcgggtt gtaaacctct tttagcaggg     420
aagaagcgaa agtgacggta cctgcagaaa aagcgccggc taactacgt                 469

<210> SEQ ID NO 2
<211> LENGTH: 728
<212> TYPE: DNA
<213> ORGANISM: Acinetobacter sp.

<400> SEQUENCE: 2
tagagtttga tcatggctca gattgaacgc tggcggcagg cttaacacat gcaagtcgag      60
cgggggaagt agcttgctac tggacctagc ggcggacggg tgagtaatgc ttaggaatct     120
gcctattagt gggggacaac attccgaaag gaatgctaat accgcatacg tcctacggga     180
gaaagcaggg gaccttcggg ccttgcgcta atagatgagc ctaagtcgga ttagctagtt     240
ggtggggtaa aggcctacca aggcgacgat ctgtagcggg tctgagagga tgatccgcca     300
cactgggact gagacacggc ccagactcct acgggaggca gcagtgggga atattggaca     360 atgggggaa ccctgatcca gccatgccgc gtgtgtgaag aaggccttat ggttgtaaag     420
cactttaagc gaggaggagg ctactagtat taatactact ggatagtgga cgttactcgc     480
agaataagca ccggctaact ctgtgccagc agccgcggta atacagaggg tgcgagcgtt     540
aatcggattt actgggcgta aagcgtgcgt aggcggccat ttaagtcaaa tgtgaaatcc     600
ccgagcttaa cttgggaatt gcattcgata ctggatggct agagtatggg agaggatggt     660
agaattccag gtgtagcggt gaaatgcgta gagatctgga ggaataccga tggcgaaggc     720
agccatct                                                             728

<210> SEQ ID NO 3
<211> LENGTH: 482
<212> TYPE: DNA
<213> ORGANISM: Bacillus sp.

<400> SEQUENCE: 3
ggacgaacgc tggcggcgtg cctaatacat gcaagtcgag cggayctctt cggagrtcag      60
cggcggacgg gtgagtaaca cgtgggcaac ctgcctgtaa gactgggata actccgggaa     120
```

```
accggagcta ataccggata ctatgtcaaa ccgcatggtt tgacattcaa agacggtttc      180
ggctgtcact tacagatggg cccgcggcgc attagctagt tggtgaggta atggctcacc      240
aaggcgacga tgcgtagccg acctgagagg gtgatcggcc acactgggac tgagacacgg      300
cccagactcc tacgggaggc agcagtaggg aatcttccgc aatggacgaa agtctgacgg      360
agcaacgccg cgtgagtgat gaaggttttc ggatcgtaaa actctgttgt cagggaagaa      420
caagtgccgg agtaactgcc ggcgccttga cggtacctga ccagaaagcc acggctaact      480
ac                                                                    482
```

MICROBIAL ENZYMES AS DETERGENT ADDITIVES

CROSS-REFERENCE TO RELATED APPLICATIONS

This Application is the U.S. National Stage filing under 35 U.S.C. §371 of PCT/IB2010/001816 filed on Jul. 24, 2010, which claims priority to Indian Patent Application Serial Number 599/KOL/2010, filed on Jun. 1, 2010, both of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 15, 2011, is named 09160520.txt and is 2,847 bytes in size.

TECHNICAL FIELD

The technology relates in part to isolated microbial amylases, lipases, and proteases suitable for use as detergent additives. The technology also relates in part to methods for removing stains using isolated microbial enzymes.

BACKGROUND

Detergents are used for cleaning various types of fabrics and hard surfaces. Enzymes, such as protease, amylase, and lipase may be used as detergent additives to improve cleaning efficiency. Protease hydrolyzes proteins into soluble amino acids. Amylase catalyzes the break down of starch-based stains into smaller segments of oligosaccharides and dextrins, which are water soluble. Lipase hydrolyzes triglycerides into mono and diglycerides, glycerol, and free fatty acids, which are more soluble than fats. These more soluble reaction products may be more easily removed from fabrics and surfaces, increasing the cleaning efficiency of the detergent used.

Natural microbial isolates may be used to produce enzymes, and these natural sources may be obtained from different environments. Urban areas sometimes dispose of waste in wetlands, and environmental samples from these waste dumps may contain a richly bio-diverse source of microbes.

SUMMARY

Provided herein are compositions that include isolated microbial enzymes, such as amylases, lipases, and proteases that are useful as detergent additives. Also provided are methods of isolating amylases, lipases, and proteases from microbes, as well as methods of using these enzymes as detergent additives, and for stain removal.

Thus featured in some embodiments are compositions including a *Bacillus* strain SV-1 amylase, where: the *Bacillus* strain SV-1 includes a 16SrDNA sequence including SEQ ID NO: 3; or representative bacteria of the strain have been deposited with the Microbial Type Culture Collection and designated by deposit accession number MTCC5567. Also provided are detergent compositions that include the enzymatic detergent additive and a surfactant, in certain embodiments.

In some embodiments, also provided are enzymatic detergent additives that include the amylase. In some embodiments, an additive is in the form of a granulate, a powder, or a liquid, and in some embodiments, the additive further includes an enzyme stabilizer. In some embodiments, the additive further includes a surfactant.

In some embodiments, also provided are additives including an amylase and further including a lipase. In some embodiments, the lipase is an *Acinetobacter* strain BS lipase; and the *Acinetobacter* strain BS includes a 16SrDNA sequence including SEQ ID NO: 2; or representative bacteria of the strain have been deposited with the Microbial Type Culture Collection and designated by deposit accession number MTCC5563.

In some embodiments, also provided are additives including an amylase and further including a protease. In some embodiments, the protease is a *Microbacterium* strain SRC-010 protease; and the *Microbacterium* strain SRC-010 includes a 16SrDNA sequence including SEQ ID NO: 1; or representative bacteria of the strain have been deposited with the Microbial Type Culture Collection and designated by deposit accession number MTCC5565.

Also provided are enzymatic detergent additives that include an amylase and a lipase, additives that include an amylase and a protease, and additives that include an amylase, a protease, and a lipase, in certain embodiments. In some embodiments, the enzymatic detergent additive further includes a surfactant. In some embodiments the enzymatic detergent additive further includes an enzyme stabilizer. In some embodiments, the enzymatic detergent additive is in the form of a granulate, a powder, or a liquid.

Also featured in some embodiments is a process for production of an amylase, including culturing a *Bacillus* strain in growth medium; removing cell-free cultured media from the culture; and purifying the amylase from the cell-free culture media; where the *Bacillus* strain includes a 16SrDNA sequence including SEQ ID NO: 3; or where representative bacteria of the *Bacillus* strain have been deposited with the Microbial Type Culture Collection and designated by deposit accession number MTCC5567. In some embodiments, the *Bacillus* strain is cultured under batch fermentation conditions, and sometimes the *Bacillus* strain is immobilized.

Also provided in some embodiments is a process for removing a stain from a surface, including contacting the stain with a *Bacillus* strain amylase herein. In some embodiments, the surface is selected from the group consisting of fabric, flooring, ceramic, glass, or metal. In some embodiments, the process further includes contacting the stain with a lipase, including contacting the stain with a lipase described herein. In certain embodiments, the process further includes contacting the stain with a protease, including contacting the stain with a described herein. In some embodiments, the process further includes contacting the stain with a lipase and with a protease, including contacting the stain with an *Acinetobacter* strain lipase or a *Microbacterium* strain protease described herein.

The foregoing summary illustrates certain embodiments and does not limit the disclosed technology. In addition to illustrative aspects, embodiments and features described above, further aspects, embodiments, and features will become apparent by reference to the drawings and the following detailed description and examples.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1:
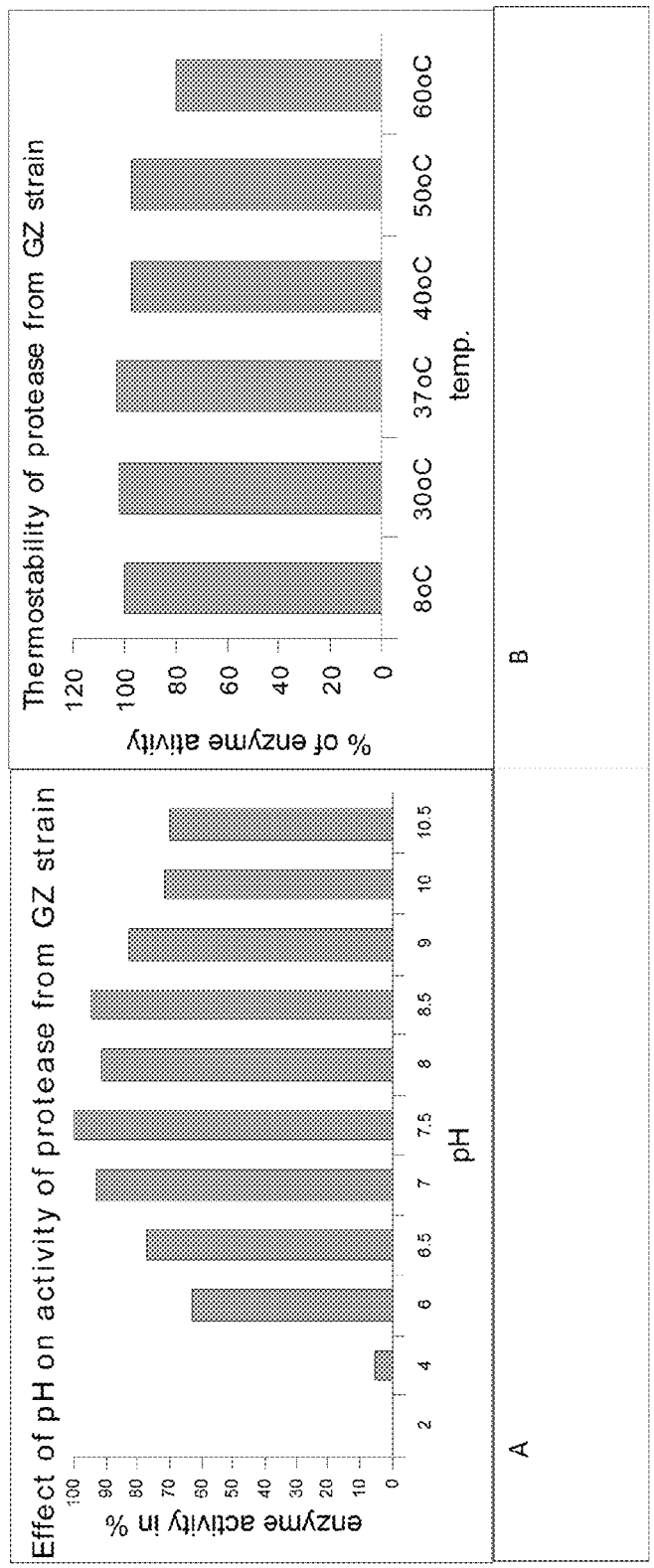
FIG. 1a is a graph representing a pH profile of the isolated protease enzyme from SRC_GZ.
FIG. 1b is a graph representing a thermostability profile of the isolated protease enzyme from SRC_GZ.

In the following detailed description, reference is made to the accompanying drawings, which form a part hereof. In the drawings, similar symbols typically identify similar components, unless context dictates otherwise. Illustrative embodiments described in the detailed description, drawings, and claims do not limit the technology. Other embodiments may be utilized, and other changes may be made, without departing from the spirit or scope of the subject matter presented herein. It will be readily understood that aspects of the present disclosure, as generally described herein, and illustrated in the drawings, can be arranged, substituted, combined, separated, and designed in a wide variety of different configurations, all of which are explicitly contemplated herein.

Enzymes may be used to improve the cleaning efficiency of detergents, including, for example, liquid, powder, and granular detergents. The performance of enzymes in detergents depends on a number of factors, such as, for example, the composition of the detergent, type of stains to be removed, wash temperature, washing procedure and wash-water hardness. Besides high temperature and alkalinity, the enzyme often must withstand the presence of detergent additives such as, for example, bleaching agents, bleach activators, surfactants, perfumes, and the like. Microbe-produced proteases can be used as detergent additives (Ganesh Kumar, C. and H. Tyagi, 1999. Microbial alkaline protease: From a bioindustrial viewpoint. Biotechnol. Adv., 17: 561-594). These enzymes hydrolyze protein-based stains in fabrics into soluble amino acids. Among the various proteases, bacterial proteases often are utilized and sometimes animal or fungal proteases are used. Bacterial proteases selected often are extracellular, readily produced in large amount and are often thermostable and active at wider pH ranges. One factor to be considered during the selection of the enzyme is its stability and the shelf life of the enzymatic action. For industrial applications, the immobilization of enzyme on a solid support can offer additional advantages like repeated use of the enzyme, ease of product separation and improvement in stability (Ahmed, S. A., et al., 2007. Stabilization of *Bacillus licheniformis* ATCC21415 alkaline protease by immobilization and modification. Aust. J. Basic *Applied Sci.*, 1 (3): 313-322).

Other enzymatic detergent additives are amylase, cellulose, and lipase. Enzymes such as amylases, proteases and lipases can improve washing efficiency. Amylase catalyzes the break down of starch based stains into smaller segments of oligosaccharides and dextrins which are water soluble. Lipase can be used in detergent formulations to remove fat-containing stains such as those resulting from frying fats, butter, salad oils etc. The enzyme hydrolyzes triglycerides into mono and diglycerides, glycerol and free fatty acids which are more soluble than fats. Protease catalyzes the breakdown of proteins into small peptides and amino acids.

Because they are often active under moderate conditions, such as warm temperatures and neutral pH, they may reduce energy consumption by eliminating the need to maintain extreme environments, as required by many chemically catalyzed reactions. The reaction specificities of the enzymes minimize the amount of by-products, and therefore may offer a lower risk to the environment than chemically catalyzed reactions.

In certain embodiments, microbial enzymes, such as protease, lipase, and amylase, are isolated from bacteria. These enzymes, alone, or in combination, may be used as detergent additives to enhance stain removal.

By "isolated" is meant that the enzyme, protein, polypeptide, or peptide, is separated from other cellular materials. For example, a protein may be isolated from bacteria by being secreted into a supernatant, and the supernatant then separated from the protein-producing bacteria. Or, for example, the protein may be further purified using additional separation techniques that would separate the protein from some other materials in the supernatant.

The term "protease" includes all proteins, polypeptides, and peptides having a protease activity, including a peptidase and/or a proteinase activity. Proteases can catalyze the hydrolysis of peptide bonds. The term "*Microbacterium* strain protease" includes proteases of *Microbacterium* origin, and may be cellular, secreted, or isolated. The protease may be isolated from cell culture using standard protease isolation methods, and the protease characteristics discussed herein.

The term "lipase" includes all proteins, polypeptides, and peptides having a lipase activity. Lipases catalyze the hydrolysis of ester bonds in water-insoluble, lipid substrates. The term "*Acinetobacter* strain lipase" includes lipases of *Acinetobacter* origin and may be cellular, secreted, or isolated. The lipase may be isolated from cell culture using standard lipase isolation methods, and the lipase characteristics discussed herein.

The term "amylase" includes all proteins, polypeptides, and peptides having an amylase activity. Amylases catalyze the breakdown of starch, such as carbohydrates, into sugars. The term "*Bacillus* strain amylase" includes amylases of *Bacillus* origin and may be cellular, secreted, or isolated. The amylase may be isolated from cell culture using standard amylase isolation methods, and the amylase characteristics discussed herein.

An article may be contacted with a detergent, additive or detergent-additive for stain removal. By "contacting" is meant that the detergent, additive, or detergent-additive formulation is brought into close contact with, including touching, a surface, such as a solid or fabric surface, such as, for example, fabric, flooring, ceramic, glass, or metal.

For example, the enzymes may be present in the composition that contacts the surface at levels from about 0.00001% to about 2% enzyme protein by weight of the composition.

In other examples, the enzymes may be present in proportions of enzyme to detergent at levels from about 3 units to about 7 units enzyme per gram detergent.

Enzyme additive formulations include enzymes that are, for example, from about 80% to about 90% free of other proteins. Where enzyme additives include more than one enzyme, the other proteins include those that are not one of the enzymes. For example, where an enzyme additive includes protease and lipase, the "other proteins" are those that are not protease or lipase.

In certain embodiments, the detergent and enzymatic detergent additive compositions include one or more enzyme stabilizers, surfactants, and/or fillers. An "enzymatic detergent additive" may include one or more enzymes selected from the group consisting of proteases, lipases, and amylases. The enzymatic detergent additive may be, for example, formulated as a powder, granulate, or a liquid. By "enzyme stabilizer" is meant a composition that increases the storage stability of an enzyme. Enzyme stabilizers may include, for example, propylene glycol, calcium chloride, glycine. By "surfactant" is meant a surface active agent, including, for example, anionic, nonionic, ampholytic, cationic, and zwitterionic surfactants, and mixtures thereof. By "filler" is meant a molecule or compound that is used to dilute or distribute the active ingredients of the detergent composition, in appropriate concentrations. Fillers may include, but are not limited to, sodium sulphate for powder cleaning compositions, and water for liquid cleaning compositions.

According to certain embodiments, the enzymatic detergent additives may be used with or incorporated into a detergent composition, such as, but not limited to, a fabric care composition, a dish cleaning composition, and a home care composition. Examples of fabric care compositions include, but are not limited to, liquid laundry detergents, solid laundry detergents, powder laundry detergents, granular laundry detergents, laundry soap products, heavy duty liquid detergents, rinse additives, laundry spray treatment products, and laundry pre-treatment products. Examples of dish cleaning compositions include, but are not limited to, hand dish washing detergents, solid granular dish soap, and automatic dish washing detergents. Examples of home care compositions include, but are not limited to, hard surface cleaning detergents, floor cleaning compositions, window cleaning compositions, toilet and bathroom cleaning compositions, car washing detergents, and rug or carpet cleaning detergents. The detergent compositions may be, for example, in granular, powder, liquid, gel, paste, bar, or flake form.

Certain proteases, amylases and lipases useful for preparing detergent additives are described in further detail hereafter.

Proteases

A particular protease enzyme was isolated from a bacterial culture (SRC_GZ) obtained from an old dumping ground [22°32' 17.5" N and 88°23' 53.7"E (using GOOGLE EARTH)] at East Calcutta Wetland, that has been converted into a recreational centre with a forest like vegetation. It is a gram negative *bacillus* that produces protease and catalase but does not secrete DNAse, lipase, oxidase, lecithinase or amylase. The molecular identification of the isolate was based on a partial sequence analysis of 16SrDNA, and the sequence is available at GenBank as *Acinetobacterium* SRC-010, with the accession number E0006695. This partial sequence shows 98.22% identity with *Microbacterium luteolum*. The bacteria is resistant to Polymyxin B (100 µg), Cloxacillin (30 µg), Rifampicin (15 µg), Cephotaxime (30 µg), Metronidazole (4 µg), Trimethoprin (30 µg) and Vancomycin (30 µg) as per the protocol of Himedia Laboratories Pvt Ltd. The sensitivity of the strains against different antibiotics was determined by disk diffusion method using commercially available (Himedia) antibiotic discs. The representative of each group of antibiotic had been tasted. The antibiotics used were Ampicillin (A10), Cephydroxil (Cq30), Chloramphenicol (C30), Cloxacillin (Cx30), Cephotaxime (Ce30), Ceftazidime (Ca30), Ciprofloxacin (Cf5), Doxycycline Hydrochloride (Do30), Gentamicin (G10), Metronidazole (Mt4), Neomycin (N30), Norfloxacin (Nx10), Polymyxin B (Pb100), Rifampicin (R15), Roxithromycin (Ro30), Tetracycline (T30), Trimethoprin (Tr30), Vancomycin (Va30). The concentrations of the antibiotics in microgram per disc were mentioned in parenthesis indicated above. Mueller Hinton Agar medium (Himedia—M173) was used to grow each of the microorganisms for antibiotic sensitivity test. The log phase culture of each isolate was diluted 100 times and poured on Mueller Hinton Agar (MHA) plates. It was swirled uniformly to distribute the culture throughout the plate. After waiting for 30 minutes, the cultures were carefully pipetted out from the plates and the plates were allowed to dry. Then the antibiotic disks were placed onto the MHA surface using the dispenser provided with the antibiotic discs. The plates were incubated at 37° C. for overnight. The zones of inhibition were measured. The results were evaluated using National Committee for Clinical Laboratory Standard's (NCCLS) chart provided with the antibiotic discs by Himedia. The assay was done thrice for each organism.

In some embodiments the protease is further characterized by: a pH optimum in the range of 6-10.5; more than 90% proteolytic activity at a temperature range of 4° C. to 50° C.; minimum inhibition (0.4%) of proteolytic activity by 5 mM of Cu and Co ions; inhibition of proteolytic activity (nearly 100%) by Cr and Pb ions; and inhibition of activity by ethylenediaminetetraacetic acid. The activity was measured as per the method of Malathu, R., et al., 2008 Characterization and Wash Performance Analysis of Microbial Extracellular. American Journal of Applied Sciences, 5 (12): 16501661.)

The isolate was found to grow in the presence of heavy metal salts like 1 mM $NiCl_2.6H_2O$, 3 mM $CoCl.6H_2O$, 1 mM $Cr_2O_3$, 2 mM $CuSO_4.5H_2O$, 2 mM $Al(NO_3)_3.9H_2O$, 6 mM $Pb(NO_3)$, 0.2 mM $HgCl_2$. This strain was found to accumulate lead (1306 ppb), copper (132.42 ppb) and chromium (81.84 ppb) and distinct nano particles were found in case of treatment with 5 ppm Pb, 0.5 ppm Cr, 2 ppm Cd, 0.1 ppm Hg and 1 ppm Cu. About 6-15 nano particles per cell were found after Pb treatment and their size varied from 10-11 nm. In case of Cr and Cu treatment, the elongation of cell size was observed which can be one of the effects of metal induced stress on cell shape so as to delay the cell division.

The protease content of cell free supernatant was determined by a protease assay using hide powder azure as substrate as discussed in Malathu, R., et al., 2008 Characterization and Wash Performance Analysis of Microbial Extracellular. American Journal of Applied Sciences, 5 (12): 1650-1661., which is hereby incorporated by reference herein. The cell free supernatant was used for enzyme quantification. Post overnight growth, the isolate GZ was found to produce about 0.4 units of protease/ml, where 1 unit of activity can be defined as the amount of enzyme required to produce an increase of 0.1 absorbance (OD at 440 nm). The protease from GZ can tolerate a wide range of from pH 6-10.5 and was found to retain 71% of its activity at pH 10.5 (FIG.

1a). The other significant feature of the enzyme was its stability at high temperatures up to 60° C. with 74.4% activity retention (FIG. 1b).

The protease activity was found to be more than 60% within the range of pH 6-10.5 and the maximum activity was evident at pH 7.5. The method used was as reported by Malathu et al. Similarly, the activity was demonstrated to be more than 90% within the range of 4° C. to 50° C. and about 80% activity observed at 60° C. Metal ions like Cu and Co exhibited minimum inhibition on the enzyme activity whereas the presence of Cr and Pb ions caused complete inhibition of enzyme activity. The metalloprotease nature of the enzyme was confirmed by the inhibition of activity by EDTA. Ionic detergent like SDS caused minimal inhibition of the activity whereas Triton X-100 caused complete inhibition. Agents like bleach, hydrogen peroxide and beta-mercaptoethanol exert significant inhibition of enzyme activity. There was complete inhibition of activity upon treatment with PMSF and Leupeptin while partial inhibition in case of TPCK, TLCK, Bestatin, EGTA, Ebalactone B and Phosphoramidone which indicated the enzyme to be a serine protease. The enzyme was found to possess the apr gene, the gene for alkaline protease.

Lipases

A particular lipase enzyme was isolated from a bacterial culture (SRC_BS) obtained from Bheri (the shallow, flat bottomed, waste water fed fish ponds) soil at East Calcutta Wetland [22°33' 12.06" N and 88°24' 41.05" E]. Natural remediation taking place in Bheri is further facilitated by the alkaline pH generated by the addition of lime which in turn causes decrease in coliform count from 23200 to 1090 (in raw sewage canal and its corresponding Bheri). There is little change in conductivity (1.6) and dissolved oxygen (3.8) among the two. (Pradhan, A., P., et al., 2008. Phytoplankton diversity as indicator of water quality for fish cultivation. American Journal of Environmental Sciences, 4(4):271276.). It is a gram negative short *bacillus*. The molecular identification of the isolate was based on a partial sequence analysis of 16SrDNA, and the sequence is available at GenBank as *Acinetobacter* sp. BS, with the accession number FJ788517. This partial sequence shows 99% identity with *Acinetobacter* sp HB1. The strain produces catalase and lipase and is Vancomycin (30 μg) and Ampicillin (10 μg) resistant. The strain does not secrete protease, oxidase, DNase, lecithinase or amylase. The isolate was found to secrete 8 units/ml of lipase after 16 hours of growth under optimum condition. Moreover the isolate was found to grow in presence of heavy metal salts like 2 ppm $NiCl_2.6H_2O$, 1 ppm $CoCl.6H_2O$, 2 ppm $Cr_2O_3$, 2 ppm $CuSO_4.5H_2O$, 6 ppm $Al(NO_3)_3.9H_2O$, 5 ppm $Pb(NO_3)$. The maximum accumulation of lipase was found with Pb salt treatment (about 1446 ppb) followed by Cu at about 300 ppb. In comparison to Pb and Cu, relatively less accumulation of lipase was found with Ni (2.036 ppb), Co (2.293 ppb) and Cu. (9.253 ppb) treatment. Metals like Ag were found to be localized inside and throughout the cell, as determined through Transmission Electron Microscopy. This isolate was also found to degrade crude oils like burnt mobil and mobil. In liquid culture with 1% inoculum and 1.5% mobil, this isolate demonstrated degradation efficiency of more than 70% and up to 90% for different individual components of the mineral oil as analyzed using GC-MS (Parkin Elmer XL with Flame ionization detect). The details of the program used are as follows: Column PE5, length 25 m, inner diameter 200 μm, film thickness 0.33 μM, Oven program including 4 min hold at 40° C. with ramping at 10° C. per min up to 320° C. followed by 8 min hold at 320° C., total run time being 40 min. The injector temperature was 200° C., split flow at 25 ml/min, helium as carrier at a flow rate of 0.7 ml/min).

Enzyme production was optimized in flask culture. About 5 units/ml of lipase enzyme was produced by the isolate BS after 16 hours of growth. One (1) unit of lipase enzyme was defined as amount of enzyme releasing 1 umole of pNitrophenol per ml per min. The cell free supernatant was used for enzyme assays. The enzyme assay for lipase was done as reported by Sarkar et al., A. K., et al., Microbial Biodiversity Screening from Mineral Ore Rich Site in Andhra Pradesh, India, 2008. Online J. Biol. Sci. 8:32-40, which is hereby incorporated by reference herein.

Amylases

Amylase enzyme was isolated from a bacterial culture (SRC_SV1) obtained from the water of the marine coast of Vizag under normal salinity [17°43'04.69" N and 83°19' 54" E (using GOOGLE EARTH)]. The molecular identification of the isolate was based on a partial sequence analysis of 16SrDNA, and the sequence is available at GenBank as *Bacillus* sp. SV1, with the accession number FJ377723. This partial sequence shows 99.91% identity with *Bacillus cibi*. The strain shows resistance to Metronidazole.

Figure 9:
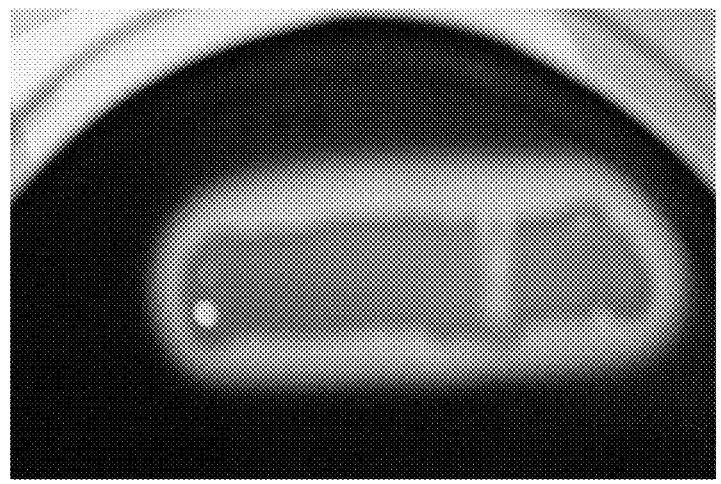
FIG. 9 is a photograph showing amylase activity on a starch-containing plate.

FIG. 9 depicts the results of an assay of amylase activity on starch residue on a plate using Himedia starch agar as per the manufacturer's instructions (HIMEDIA LABORATORIES. PVT. LTD.). The extracellular supernatant was used as the source of amylase.

Enzyme Production

Enzymatic detergent additive-producing strains may be used to secrete the additives by any available methods, including, for example, by batch fermentation and by immobilization of the microbes. Fermentation can be conducted and controlled by various techniques. Appropriate nutrient cultures may be prepared, including, for example, carbon and nitrogen sources and other nutritional substances that favor or are necessary for the growth of the particular microbes (e.g., bacteria). Sugars and sugar-containing substances may be included as suitable sources of carbon, including, for example, but not limited to, starch, dextrin, cane sugar, lactose, maltose, fructose, and glucose. Nitrogen sources include, for example, protein-containing substances, such as peptone from soy beans, meat, casein, gelatin, yeast protein or yeast extract, wastes from the processing of meat or animal bodies, and ammonium salts. Other examples of nutrients include, for example, inorganic salts, for example alkaline and alkali earth metal salts and phosphates, together with trace elements, such as, for example, Fe, Mg, Mn, Co, and Ni.

Fermentation may be carried out at appropriate pH levels and temperatures to maximize microbe growth and secretion of enzyme, including, for example, at pH levels between about 5 and 9, or, for example, at pH levels between about 6 and 8. The temperature may be, for example, between about 33 to about 45 degrees Celsius, or, for example, between about 35 to about 39 degrees Celsius, or, for example, at about 37 degrees Celsius.

Enzyme may also be produced using immobilized microbial cells, for example, as presented in Kumar, S. R. and M. Chandrasekharan, 2003. Continuous production of L-glutaminase by an immobilized marine *Pseudomonas* sp BTMS-51 in a packed bed reactor. Process Biochem., 38: 1431-1436.

The cells were immobilized both in alginate beads as well as on boiled straw packed in plastic perforated containers which were in turn placed inside bigger containers with medium for microbial growth.

Enzyme Additive Formulation

Enzyme additives may be provided alone, or in detergent compositions. For example, protease, lipase, or amylase may each be formulated as separate additive compositions, including, for example, stabilizers or fillers. These compositions may be provided in liquid, powder, or granulate form. The enzyme additives may also, for example, include the enzymes in combination, for example, protease and lipase, protease and amylase, amylase and lipase, or protease, lipase and amylase. These additives may also include other enzyme additives. Detergent compositions may comprise the enzyme additives. The enzyme additives may further be provided in the form of a kit, including instructions regarding, for example, the use of the additives to remove stains, recommended washing conditions, or the proportions of additive and detergent to be used. The enzyme additive may be in a container, such as, for example, a tube, dissolvable packet, vial, pouch, or other container, and may, for example, be in a powder, granular, liquid, or other form. Kits may include more than one enzyme additive, for example, the kit may include both protease and lipase additives, and the protease and lipase additives may be provided in separate containers, or may be provided in the same container. The kit may further provide a detergent composition.

EXAMPLES

The examples set forth below illustrate certain embodiments and do not limit the disclosed technology.

Example 1

Proteases as Detergent Additives

Figure 2:
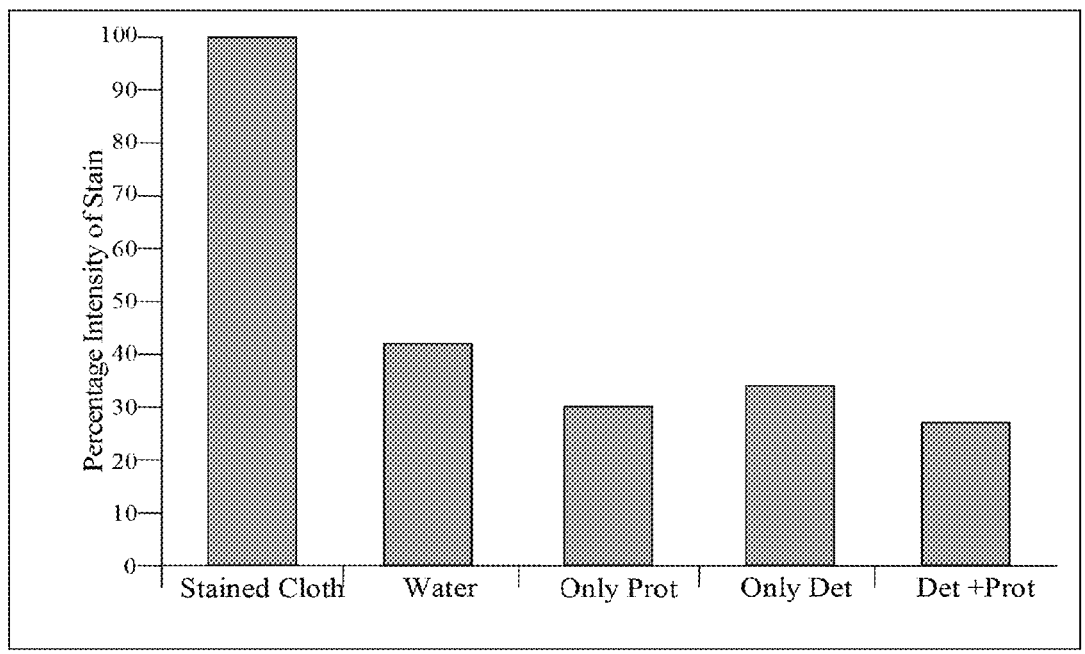
FIG. 2 is a graph representing a wash performance analysis of stain intensity, with and without addition of protease to detergent.

Protease isolated from strain SRC_GZ, added to detergent, enhanced stain removal. The protease was mixed with standard detergent, including Blue Bird detergent as well as others noted herein at a proportion of 6 units of enzyme/gm of detergent. Cloth pieces of 1.5×1.5 inches were stained with grease car door, car battery, and/or car engine grease, and kept for an hour before incubation with detergent. The cloth pieces were dipped in different combinations as stated: 1) only water (considered as negative control), 2) only detergent, 3) detergent enzyme mixture and 4) only enzyme. In the graph, Prot stands for Protease, Det stands for Detergent while Det+Prot stands for detergent with protease. The washing efficiency was evaluated after one hour of treatment by observing the stain removal after simple rubbing and rinsing with water. The extent of stain removal was analyzed by densitometric scanning of the residual stain on the cloth using software Quantity 1 from Bio-Rad. The protease treatment was found to have a better cleaning efficiency (70% stain removal) than just detergent (68% stain removal) but the best efficiency was obtained on mixing both the detergent and the protease (74% stain removal) (FIG. 2).

Figure 3:
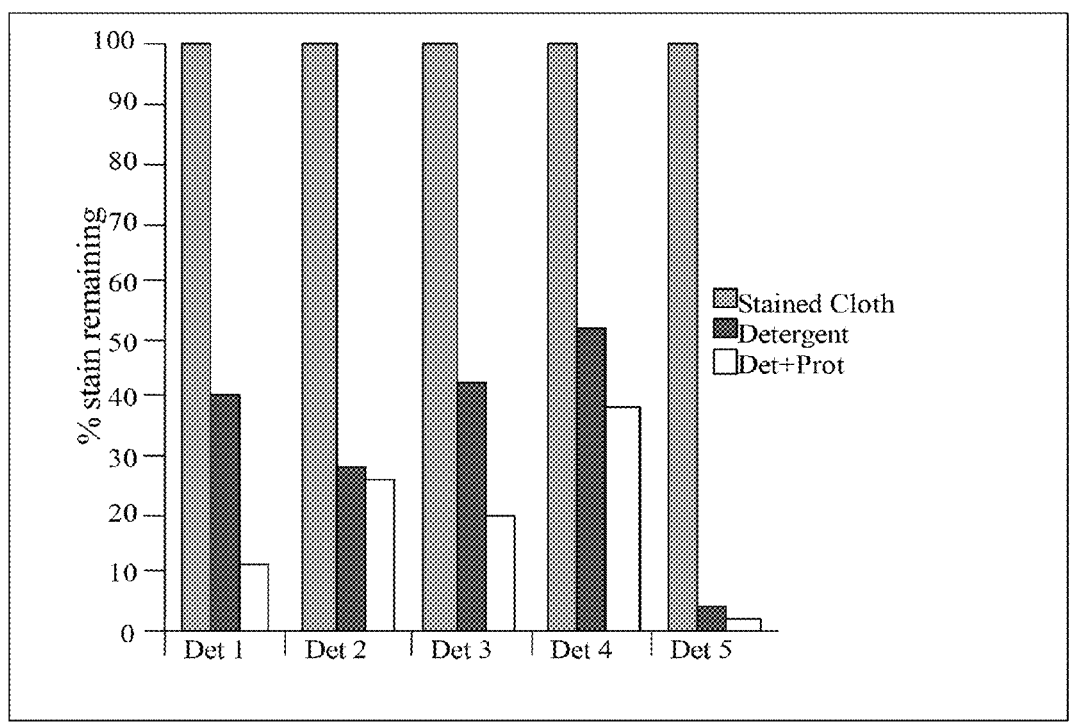
FIG. 3 is a graph representing a wash performance analysis of stain density, with and without addition of protease to different detergents.

The protease additive was compatible with different detergents. Protease enzyme at the same concentration (6 unit/gm of detergent) was mixed with different detergents available in commercial markets, namely SURF, EXCEL (Hindustan Lever Limited, Mumbai, India), TIDE (Procter and Gamble, USA), AERIAL (Procter and Gamble, USA), SUNLIGHT (Unilever, South Africa), NIRMA (Nirma Ltd., Ahmedabad, India), SAGAR (AMOCHEM, Kolkata, India), BLUE BIRD (Local Make, Kolkata, India), JET (Hindustan Chemical Company, Kolkata, India), SODA (local make, Kolkata, India), and VIM (Hindustan Lever Limited, India). FIG. 3 shows the enhancement of cleaning efficiency when adding the protease to various detergents. The stain density before washing was considered as 100%, and after washing, the remaining stain was compared for the various detergents, with or without the protease enzyme additive.

Figure 4:
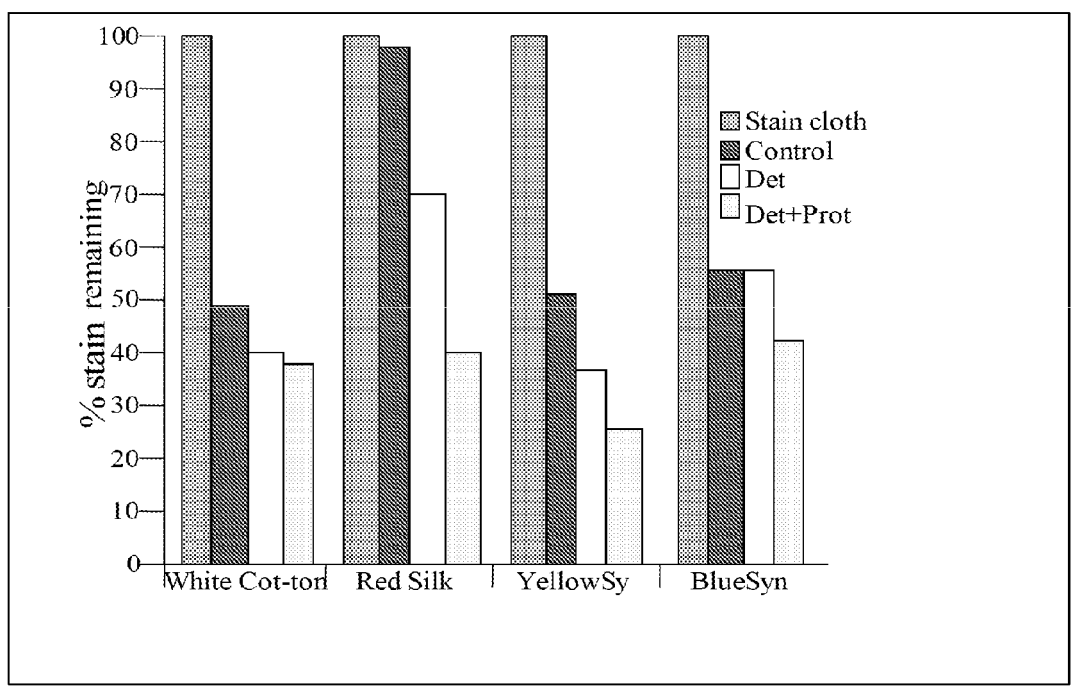
FIG. 4 is a graph representing a wash performance analysis of various fabrics, with and without addition of protease to detergent.
Figure 5:
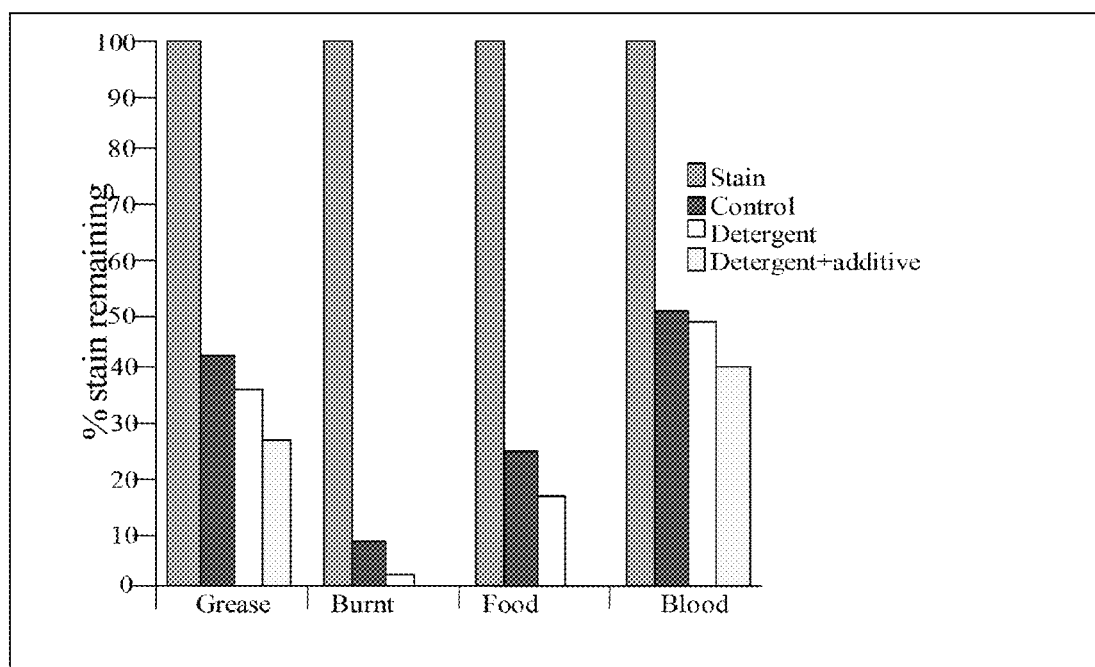
FIG. 5 is a graph representing a wash performance analysis of various types of stains, with and without addition of protease to detergent.

The effect of the enzyme as a detergent additive on various stains on different fabrics such as cotton, silk, chiffons, and synthetic material was assayed, with the results shown in FIG. 4. The x-axis represents the different fabrics used while y-axis represents the percent of residual stain post wash as compared to just stained cloth taken as 100%. FIG. 5 demonstrates that the protease addition increased the stain removal efficiency for removing stains like grease, burnt mobile, vegetable curry and blood. FIG. 5 represents the effect of the protease additive on the cleaning efficiency of various stains as obtained by densitometric scanning. The x-axis shows the different sources of stain and the y-axis represents the percent of residual stain post wash as compared to unwashed stain, considered as 100%.

Figure 6:
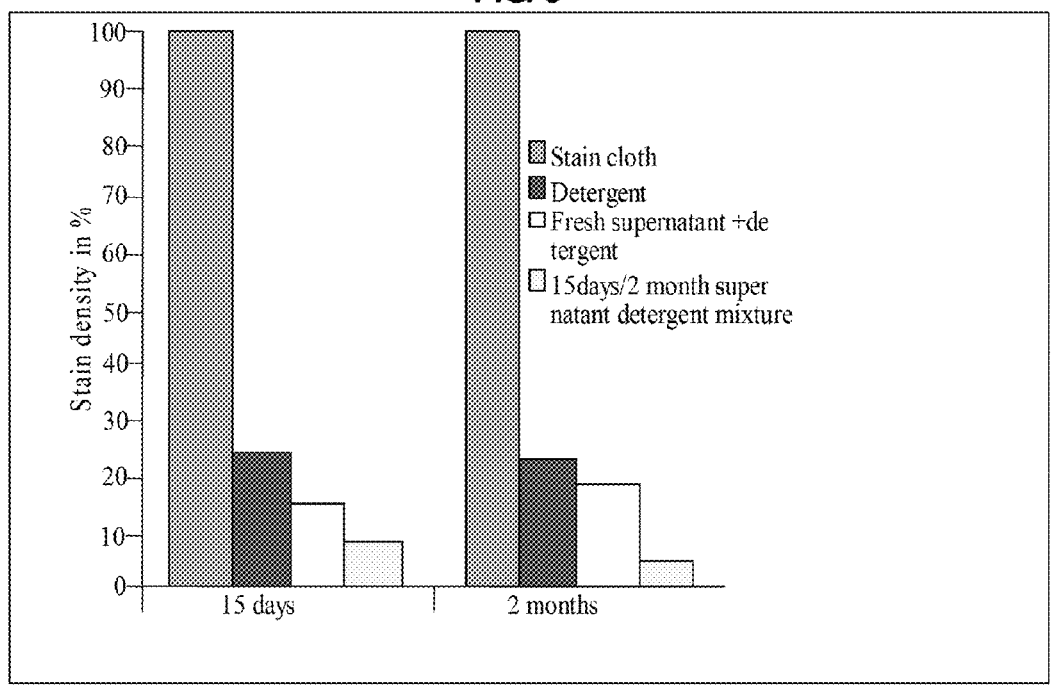
FIG. 6a is a graph representing an analysis of the shelf life of a protease additive and detergent mixture.
FIG. 6b is a photograph showing an analysis of the shelf life of a protease additive and detergent mixture.
Figure 6:
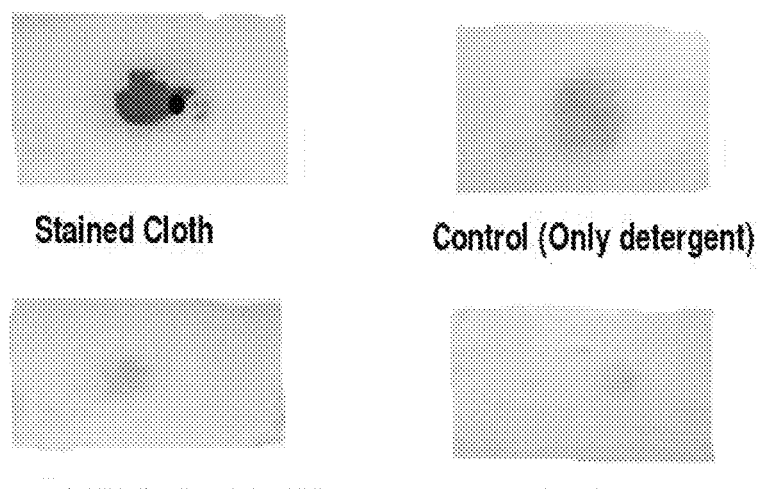

The intact activity of the protease enzyme as a detergent additive was found for a period of two months (FIG. 6a, 6b). The residual activity could be traced back after more than a year.

Example 2

Repeated Cycling of Immobilized Cells for Enzyme Production

Figure 7:
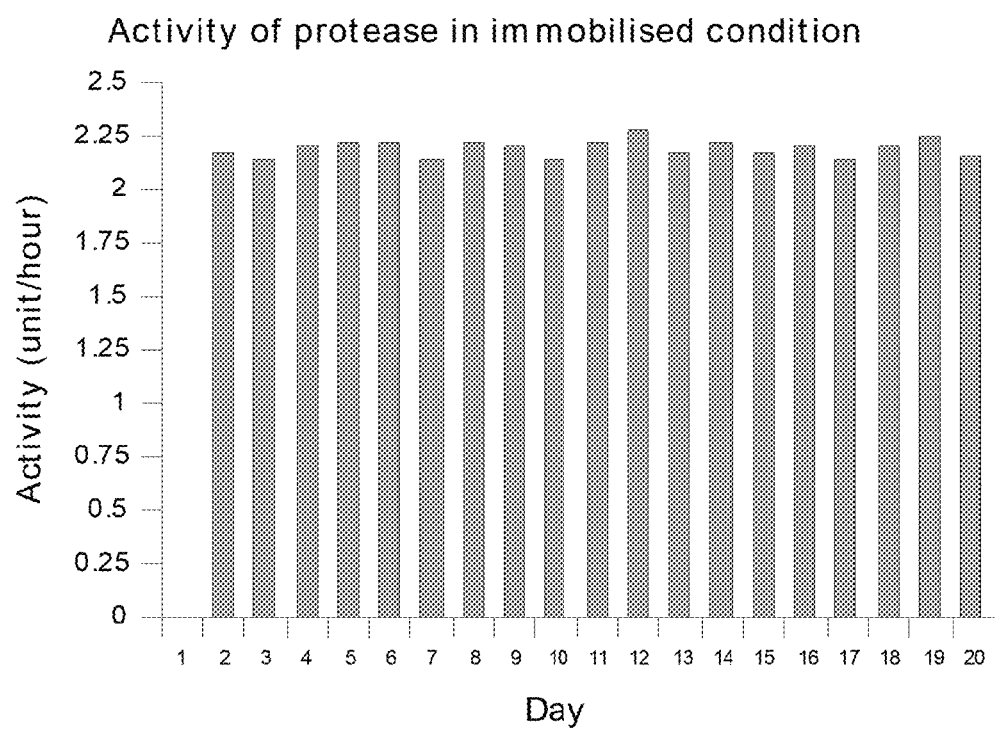
FIG. 7 is a graph representing an analysis of protease activity obtained from immobilized cells over time.

Immobilized SRC_GZ bacteria was used to produce protease using methods essentially as presented in Kumar, S. R. and M. Chandrasekharan, 2003. Continuous production of L-glutaminase by an immobilized marine *Pseudomonas* sp BTMS-51 in a packed bed reactor. Process Biochem., 38: 1431-1436. The protease-producing cells were immobilized in 8% Na-alginate solution and 1M $CaCl_2$. The enzyme produced upon immobilization of cells (1% inoculum) demonstrated a higher efficiency when used to clean stains when in a shaking condition (1 U/ml activity) when the supernatant was compared to a stationary condition (0.5 U/ml activity). The enzyme production was relatively stable throughout the 20 cycles both for static and shaking conditions. (FIG. 7).

Example 3

Lipase Increases the Efficiency of Detergent Additives Including Protease

Figure 8:
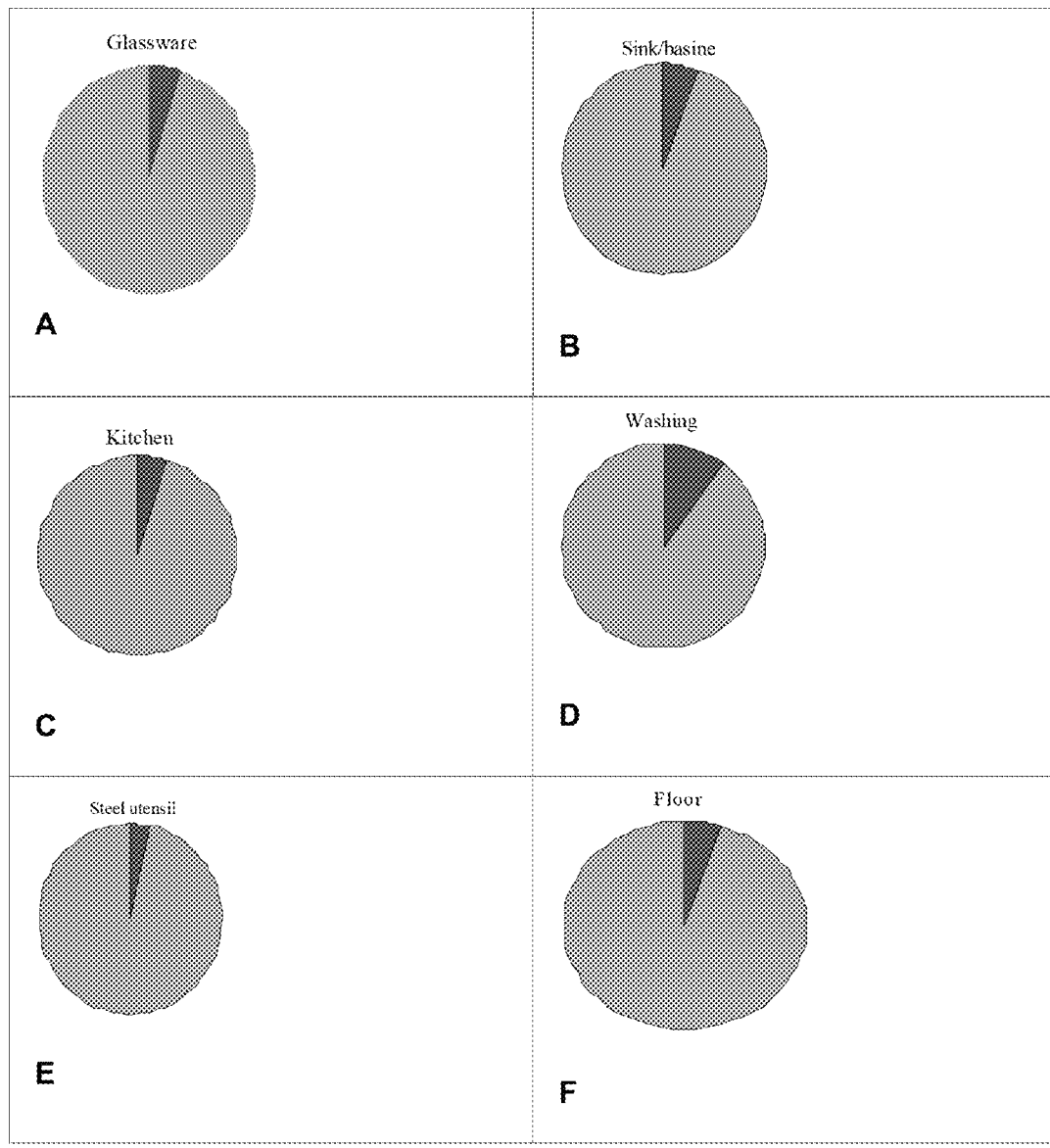
FIGS. 8a-8f are charts representing market survey results depicting the acceptability of a detergent formulation including protease and lipase additives where the darker shade depicts the percentage of activity.

Adding bacterial lipase to detergent and protease additive increases the efficiency of stain removal. Lipase production was done under shake flask conditions at 37° C. with continuous shaking at 150 rpm. The standard combination was addition of 3 ml (24 units) of extracellular supernatant containing lipase to 0.25 gm of detergent containing 6 units of protease/gm of detergent. A market survey was conducted to determine the acceptability of the formulated detergent. As shown in FIG. 8, the formulated detergent was acceptable to the survey participants. The sample size for the three separate survey were 34, 37, and 31 families respectively from different strata of the society) There was 90% acceptance for use in washing cloths, 96.6% for washing steel utensil, 95.23% accepted the formulation for washing kitchens, 96.42% for washing glassware, 95.5% for washing floors, 90% accepted for cleaning commode/tiles and 94.4% accepted the detergent formulation for washing sink and basins (FIGS. 8a-8f).

Example 4

Amylase Increases the Efficiency of Detergent Additives Including Protease and Lipase Adding bacterial amylase to detergent, supplemented with protease and lipase additives, further increases the efficiency of stain removal.

Figure 10:
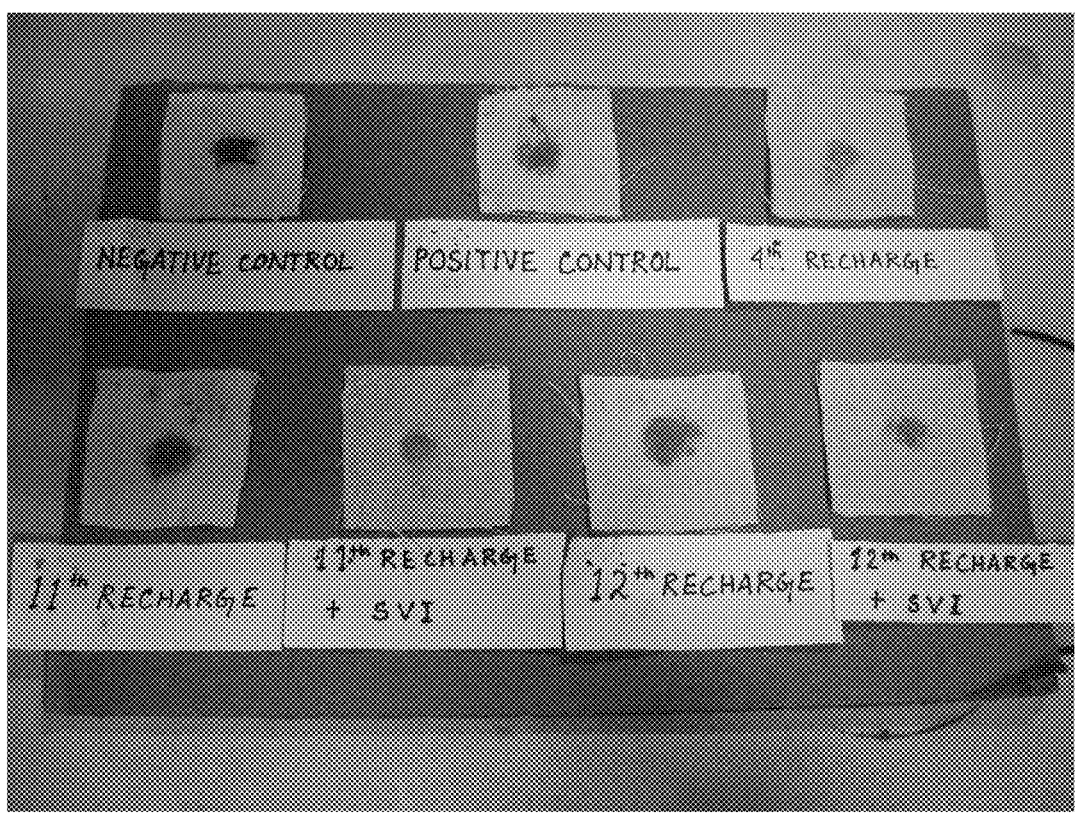
FIG. 10 is a photograph showing a wash performance analysis of stained cloth treated with protease, lipase, and amylase as detergent additives. The enzymes were produced using packed bed reactors.

3 ml of cell-free SRC-SV1 supernatant was added to 0.25 gm of detergent containing lipase (24 units) and protease (6 units/gm). It enhanced the cleaning efficiency several fold, as shown in FIG. 10. The top panel represents the following from left to right: the negative control represents stain washed in water; positive control was washed with 0.25 gm of detergent; washed with supernatant from the fourth recharge of the packed bed bioreactor. The bottom panel from left to right were as follows: washed with supernatant from the 11$^{th}$ recharge; washed with supernatant from the 11$^{th}$ recharge along with 3 ml of amylase; washed with supernatant from the 12$^{th}$ recharge; and washed with supernatant from the 12$^{th}$ recharge along with 3 ml of amylase.

Example 5

16SrDNA Sequences of Bacteria Used for Isolation and Identification of Enzymes This example provides 16SrDNA sequences of protease, lipase, and amylase, as deposited in GenBank.

```
                                                           SEQ ID NO: 1
Microbacterium SRC 010 (Deposit Accession number MTCC
5565) 16S ribosomal RNA gene, partial sequence
    1 ggatgaacgc tggcggcgtg cttaacacat gcaagtcgaa cggtgaagca ggagcttgct 61 cttgtggatc agtggcgaac gggtgagtaa cacgtgagca acctgcccct gactctggga 121 taagcgctgg aaacggcgtc taatactgga tatgtgacgt gaccgcatgg tctgcgtttg 181 gaaagatttt tcggttgggg atggctcgc ggcctatcag cttgttggtg aggtaatggc 241 tcaccaaggc gtcgacgggt agccggcctg agagggtgac cggccacact gggactgaga 301 cacggcccag actcctacgg gaggcagcag tggggaatat tgcacaatgg gcgaaagcct 361 gatgcagcaa cgccgcgtga gggatgacgg ccttcgggtt gtaaacctct tttagcaggg 421 aagaagcgaa agtgacggta cctgcagaaa aagcgccggc taactacgt SEQ ID NO: 2
Acinetobacter sp. BS (Deposit Accession number MTCC 5563)
16S ribosomal RNA gene partial sequence
    1 tagagtttga tcatggctca gattgaacgc tggcggcagg cttaacacat gcaagtcgag 61 cgggggaagt agcttgctac tggacctagc ggcggacggg tgagtaatgc ttaggaatct 121 gcctattagt gggggacaac attccgaaag gaatgctaat accgcatacg tcctacggga 181 gaaagcaggg gaccttcggg ccttgcgcta atagatgagc ctaagtcgga ttagctagtt 241 ggtggggtaa aggcctacca aggcgacgat ctgtagcggg tctgagagga tgatccgcca 301 cactgggact gagacacggc ccagactcct acgggaggca gcagtgggga atattggaca 361 atgggggaa ccctgatcca gccatgccgc gtgtgtgaag aaggccttat ggttgtaaag 421 cactttaagc gaggaggagg ctactagtat taatactact ggatagtgga cgttactcgc 481 agaataagca ccggctaact ctgtgccagc agccgcggta atacagaggg tgcgagcgtt 541 aatcggattt actgggcgta aagcgtgcgt aggcggccat ttaagtcaaa tgtgaaatcc 601 ccgagcttaa cttgggaatt gcattcgata ctggatggct agagtatggg agaggatggt 661 agaattccag gtgtagcggt gaaatgcgta gagatctgga ggaataccga tggcgaaggc 721 agccatct SEQ ID NO: 3
Bacillus SV-1 (Deposit Accession number MTCC 5567) 16S
ribosomal RNA gene partial sequence
    1 ggacgaacgc tggcggcgtg cctaatacat gcaagtcgag cggayctctt cggagrtcag 61 cggcggacgg gtgagtaaca cgtgggcaac ctgcctgtaa gactgggata actccgggaa 121 accggagcta ataccggata ctatgtcaaa ccgcatggtt tgacattcaa agacggtttc 181 ggctgtcact tacagatggg cccgcggcgc attagctagt tggtgaggta atggctcacc 241 aaggcgacga tgcgtagccg acctgagagg gtgatcggcc acactggac tgagacacgg 301 cccagactcc tacgggaggc agcagtaggg aatcttccgc aatggacgaa agtctgacgg
```

```
-continued
361 agcaacgccg cgtgagtgat gaaggttttc ggatcgtaaa actctgttgt cagggaagaa 421 caagtgccgg agtaactgcc ggcgccttga cggtacctga ccagaaagcc acggctaact 481 ac
```

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

The present disclosure is not to be limited in terms of particular embodiments described in this disclosure, which are illustrations of various aspects. Many modifications and variations can be made without departing from the spirit and scope of the disclosure, as will be apparent to those skilled in the art. Functionally equivalent methods and apparatuses within the scope of the disclosure, in addition to those enumerated herein, will be apparent to those skilled in the art from the foregoing descriptions. Such modifications and variations fall within the scope of the appended claims. The present disclosure is to be limited only by the terms of claims (e.g., the claims appended hereto) along with the full scope of equivalents to which such claims are entitled. It is to be understood that this disclosure is not limited to particular methods, reagents, compounds compositions or biological systems, which can, of course, vary. It is also to be understood that terminology used herein is for the purpose of describing particular embodiments only, and is not necessarily limiting.

With respect to the use of substantially any plural and/or singular terms herein, those having skill in the art can translate from the plural to the singular and/or from the singular to the plural as is appropriate to the context and/or application. Various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Thus, it should be understood that although the present technology has been specifically disclosed by representative embodiments and optional features, modification and variation of the concepts herein disclosed may be resorted to by those skilled in the art, and such modifications and variations are considered within the scope of this technology. As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not limiting, with the true scope and spirit of certain embodiments indicated by the following claims.

What is claimed is:

1. A composition comprising a *Bacillus* strain SV-1 amylase, a *Microbacterium* strain SRC-010 protease, and a detergent, wherein
the *Bacillus* strain SV-1 comprises a 16S rDNA sequence comprising SEQ ID NO: 3; and
wherein the *Bacillus* strain SV-1 has been deposited with the Microbial Type Culture Collection and designated by deposit accession number MTCC5567; and
the *Microbacterium* strain SRC-010 comprises a 16S rDNA sequence comprising SEQ ID NO: 1; and wherein the *Microbacterium* strain SRC-010 has been deposited with the Microbial Type Culture Collection and designated by deposit accession number MTCC5565.

2. The composition of claim 1, further comprising an enzyme stabilizer.

3. The composition of claim 1, further comprising a surfactant.

4. The composition of claim 1, further comprising a lipase.

5. The composition of claim 4, wherein
the lipase is an *Acinetobacter* strain BS lipase; and
the *Acinetobacter* strain BS comprises a 16S rDNA sequence comprising SEQ ID NO: 2; or
the *Acinetobacter* strain BS has been deposited with the Microbial Type Culture Collection and designated by deposit accession number MTCC5563.

6. A composition comprising:
a *Bacillus* strain SV-1 amylase, wherein the *Bacillus* strain SV-1 comprises a 16S rDNA sequence comprising SEQ ID NO: 3 and the *Bacillus* strain SV-1 is deposited with the Microbial Type Culture Collection and designated by deposit accession number MTCC5567;
an *Acinetobacter* strain BS lipase, wherein the *Acinetobacter* strain BS comprises a 16S rDNA sequence comprising SEQ ID NO: 2 and the *Acinetobacter* strain BS is deposited with the Microbial Type Culture Collection and designated by deposit accession number MTCC5563;
a *Microbacterium* strain SRC-010 protease, wherein the *Microbacterium* strain SRC-010 comprises a 16S rDNA sequence comprising SEQ ID NO: 1 and the *Microbacterium* strain SRC-010 is deposited with the Microbial Type Culture Collection and designated by deposit accession number MTCC5565; and
a detergent.

7. The composition of claim 6, further comprising a surfactant.

8. The composition of claim 6, further comprising an enzyme stabilizer.

* * * * *